(12) United States Patent
Lee et al.

(10) Patent No.: US 9,086,409 B2
(45) Date of Patent: Jul. 21, 2015

(54) IMMUNOASSAY BIOCHIP

(75) Inventors: Gwo-Bin Lee, Tainan (TW); Huan-Yao Lei, Tainan (TW); Yu-Fang Lee, Tainan (TW); Kang-Yi Lien, Tainan (TW)

(73) Assignee: NATIONAL CHENG KUNG UNIVERSITY, Tainan (TW)

( * ) Notice: Subject to any disclaimer, the term of this patent is extended or adjusted under 35 U.S.C. 154(b) by 968 days.

(21) Appl. No.: 12/659,422

(22) Filed: Mar. 9, 2010

(65) Prior Publication Data
US 2010/0248258 A1  Sep. 30, 2010

(30) Foreign Application Priority Data

Mar. 20, 2009  (TW) ............................... 98109045 A

(51) Int. Cl.
*G01N 33/543* (2006.01)

(52) U.S. Cl.
CPC .................. *G01N 33/54386* (2013.01)

(58) Field of Classification Search
None
See application file for complete search history.

(56) References Cited

U.S. PATENT DOCUMENTS

| 7,378,280 | B2* | 5/2008 | Quake et al. ..................... 436/63 |
| 8,220,494 | B2* | 7/2012 | Studer et al. ................... 137/833 |
| 2002/0119482 | A1* | 8/2002 | Nelson et al. ..................... 435/6 |
| 2005/0092662 | A1* | 5/2005 | Gilbert et al. ................... 210/97 |
| 2005/0284817 | A1* | 12/2005 | Fernandez et al. ............. 210/695 |
| 2009/0181411 | A1* | 7/2009 | Battrell et al. ............... 435/7.92 |

* cited by examiner

*Primary Examiner* — Ann Lam
(74) *Attorney, Agent, or Firm* — Bacon & Thomas, PLLC

(57) ABSTRACT

The present invention is about a microfluidic chip for rapid detection of different target proteins and a method for using the same. The microfluidic chip utilizes antibody-conjugated magnetic beads to bind to the target proteins to form a magnetic complex, and then use the signal labeled-antibodies that can recognize said magnetic complex. Purifying said magnetic complex by the micro-magnetic field on biochip, and introducing said purified magnetic complex into the fluorescent detection area on the chip to detect the amount of the target protein in said purified complex immediately.

15 Claims, 9 Drawing Sheets

IMMUNOASSAY BIOCHIP

BACKGROUND OF THE INVENTION

1. Field of the Invention

The present invention relates to a microfluidic biochip, and more particularly, to a microfluidic biochip which integrates microfluidic device components with a special design.

2. Description of the Related Art

In recent years, severe infectious diseases, such as SARS (severe acute respiratory syndrome), have caused devastation and death throughout the world; as a result, concerns over rapid diagnosis of diseases have been raised. In the past, researchers had to practice complicated processes to obtaining biochemical test results. Thanks to the development of the ELISA (enzyme-linked immunosorbent assay) serological tests, there was a remarkable breakthrough in immediate diagnosis of an infectious disease; since then, it has been able to obtain biochemical test results relating to diagnosis of a disease within a few days. ELISA serological tests are used to detect antigen-antibody reactions in a serum sample mainly by detecting two kinds of immunoglobulins: immunoglobulin G (IgG) and immunoglobulin M (IgM). Generally, the presence of IgM in a great number is often detected at the early stage of infection, and IgG is present at the later stage, serving as a sign of past infection.

So far, the ELISA is the most common method used in the diagnosis of some virus-related infections. This assay method is based on the specificity in antigen-antibody reactions. In brief, an enzyme is linked to an antigen or antibody to form a bound complex and the bound complex will then bond to a specific antibody or antigen to become a detectable complex. Nonetheless, the whole operation process of an ELISA is labor-intensive and time-consuming. Moreover, the detection of the signs of infection, such as IgM and IgG, requires separate operation processes using an ELISA; IgM and IgG detection results cannot be obtained simultaneously. If more signs of disease activity are required through ELISA tests, it will need to consume a lot more clinical samples to be used in separate operation processes. Furthermore, manual operations tend to increase instabilities during an assay and reduce reliabilities of the acquired data.

There is no exact definition or classification with respect to a biochip. Generally, a biochip is a miniaturized instrument arranged on a substrate, which may be formed by a silicon chip, glass or a polymeric material for example, and utilizes miniaturization technology to integrate techniques in the fields of micro-electro-mechanical system (MEMS), opto-electronics, chemistry, biochemistry, medical engineering, and molecular biology technologies, etc., in order to perform tests for purposes associated with medical examination, environmental analysis, food testing and analysis, development of a new medicine, fundamental research, military defense, chemical synthesis, and so on. Biochips now available on the market are typically classified into three groups: gene chip, protein chip, and lab-on-a-chip. A so-called lab-on-a-chip may be designed according to different needs in order to have various reactions performed on a microchip. It's well known that biochemical reactions which can be performed on a lab-on-a-chip device include polymerase chain reactions (PCRs), DNA sequencing reactions, microfluidic operations, electrophoreses, mass spectrometries (MSs), antigen-antibody reactions, and common enzyme reactions.

A microfluidic biochip that is fabricated using MEMS technologies provides several advantages. It can achieve high examination efficacy, consumes few clinical samples and low energy, is compact in size and requires low fabrication cost. In particular, a microfluidic biochip that is designed to integrate microfluidic systems and detection device on a biochip has a great commercial potential and market value: complicated and expensive assay equipments can be replaced by a single, compact biochip to perform the entire assay functions.

Accordingly, an object of the present invention is to provide a microfluidic biochip having a special design to integrate microfluidic device components, so that rapid detections of complicated clinical samples can be performed on the biochip.

SUMMARY OF THE INVENTION

In view of the drawbacks of conventional assay methods, an object of the present invention is to provide a microfluidic biochip having a special design to integrate microfluidic device components, so that rapid detections of complicated clinical samples can be performed on the biochip.

In accordance with the objects stated above, the present invention provides an immunoassay biochip comprising: a mixing chamber; a mixer for mixing a fluid in the mixing chamber; a purification chamber; a first fluidic channel for connecting the mixing chamber and the purification chamber; a first bidirectional fluidic channel control unit for controlling the flow directions of a fluid in the first fluidic channel; a magnetic field generating unit for attracting magnetic matters in the purification chamber; a fluorescence detection unit, which comprises a fluorescence detection fluidic channel, a fluorescence detection area and a unidirectional fluidic channel control unit, wherein the fluorescence detection fluidic channel is used for connecting the purification chamber and the fluorescence detection area, and the unidirectional fluidic channel control unit is used for controlling the flow direction of a fluid in the fluorescence detection fluidic channel so that the fluid flows from the purification chamber into the fluorescence detection area; a waste fluidic channel having one end connected to the purification chamber; and a waste fluidic channel control unit for directing a waste fluid in the purification chamber to flow off via the waste fluidic channel.

In a further aspect, the present invention provides another immunoassay biochip comprising: a mixing chamber; a mixer for mixing a fluid in the mixing chamber; a purification chamber; a first fluidic channel for connecting the mixing chamber and the purification chamber; a first bidirectional fluidic channel control unit for controlling the flow directions of a fluid in the first fluidic channel; a magnetic field generating unit for attracting magnetic matters in the purification chamber; a storage chamber; a second fluidic channel for connecting the mixing chamber and the storage chamber; a second bidirectional fluidic channel control unit for controlling the flow directions of a fluid in the second fluidic channel; at least two fluorescence detection units, which respectively comprises a fluorescence detection fluidic channel, a fluorescence detection area and a unidirectional fluidic channel control unit, wherein the fluorescence detection fluidic channel is used for connecting the purification chamber and the fluorescence detection area, and the unidirectional fluidic channel control unit is used for controlling the flow direction of a fluid in the fluorescence detection fluidic channel so that the fluid flows from the purification chamber into the fluorescence detection area; a waste fluidic channel having one end connected to the purification chamber; and a waste fluidic channel control unit for directing a waste fluid in the purification chamber to flow off via the waste fluidic channel.

In an additional aspect, the present invention provides a method of using the immunoassay biochip of the present invention, including the steps of: (a) loading a sample and a solution containing a magnetic bead into the mixing chamber and then operating the mixer to mix the sample with the solution in the mixing chamber, wherein the magnetic bead is conjugated with a capture antibody for identifying and capturing a target; (b) operating the first bidirectional fluidic channel control unit so that the fluid mixed in step (a) flows into the purification chamber; (c) switching on the magnetic field generating unit so that the magnetic bead contained in the fluid in the purification chamber of step (b) is attracted onto the inner wall of the purification chamber; (d) operating the waste fluidic channel control unit so that the fluid in the purification chamber of step (c) flows off via the waste fluidic channel; (e) loading a resuspension solution into the purification chamber and switching off the magnetic field generating unit so that the magnetic bead is resuspended in the resuspension solution; (f) operating the first bidirectional fluidic channel control unit so that the resuspension solution flows into the mixing chamber via the first fluidic channel; (g) loading a solution containing a fluorescent antibody into the mixing chamber and operating the mixer to mix the solution with the resuspenstion solution in the mixing chamber, wherein the fluorescent antibody is labeled with a fluorescent molecule and can bind to the target; (h) operating the first bidirectional fluidic channel control unit so that the fluid mixed in step (g) flows from the mixing chamber into the purification chamber; (i) switching on the magnetic field generating unit so that the magnetic bead contained in the fluid in the purification chamber of step (h) is attracted onto the inner wall of the purification chamber; (j) operating the waste fluidic channel control unit so that the fluid in the purification chamber flows off via the waste fluidic channel; (k) loading a resuspension solution into the purification chamber and switching off the magnetic field generating unit so that the magnetic bead is resuspended in the resuspension solution; (l) operating the unidirectional fluidic channel control unit of the fluorescence detection unit so that the resuspension solution flows from the purification chamber into the fluorescence detection area via the fluorescence detection fluidic channel; and (m) conducting a fluorescence detection to determine whether the sample contains a target.

In a further aspect, the present invention provides another method of using the immunoassay biochip of the present invention, including the steps of: (a) loading a sample and a solution containing magnetic beads into the mixing chamber and then operating the mixer to mix the sample with the solution in the mixing chamber, wherein the magnetic beads are conjugated with capture antibodies for identifying and capturing a first target and a second target; (b) operating the first bidirectional fluidic channel control unit so that the fluid mixed in step (a) flows into the purification chamber; (c) switching on the magnetic field generating unit so that the magnetic beads contained in the fluid in the purification chamber of step (b) are attracted onto the inner wall of the purification chamber; (d) operating the waste fluidic channel control unit so that the fluid in the purification chamber of step (c) flows off via the waste fluidic channel; (e) loading a resuspension solution into the purification chamber and switching off the magnetic field generating unit so that the magnetic beads are resuspended in the resuspension solution; (f) operating the first bidirectional fluidic channel control unit so that the resuspension solution flows into the mixing chamber via the first fluidic channel; (g) operating the second bidirectional fluidic channel control unit so that part of the fluid in the mixing chamber flows into the storage chamber; (h) loading a solution containing a first fluorescent antibody into the mixing chamber and operating the mixer to mix the solution with the fluid in the mixing chamber, wherein the first fluorescent antibody is labeled with a fluorescent molecule and can bind to the first target; (i) operating the first bidirectional fluidic channel control unit so that the fluid mixed in step (h) flows from the mixing chamber into the purification chamber; (j) switching on the magnetic field generating unit so that the magnetic beads contained in the fluid in the purification chamber of step (i) are attracted onto the inner wall of the purification chamber; (k) operating the waste fluidic channel control unit so that the fluid in the purification chamber flows off via the waste fluidic channel; (l) loading a resuspension solution into the purification chamber and switching off the magnetic field generating unit so that the magnetic beads are resuspeneded in the resuspension solution; (m) operating the unidirectional fluidic channel control unit of one of the at least two fluorescence detection units so that the resuspension solution flows from the purification chamber into the fluorescence detection area via the fluorescence detection fluidic channel; (n) operating the second bidirectional fluidic channel control unit so that the fluid in the storage chamber of step (g) flows from the storage chamber into the mixing chamber; (o) loading a solution containing a second fluorescent antibody into the mixing chamber and operating the mixer to mix the solution with the fluid in the mixing chamber, wherein the second fluorescent antibody is labeled with a fluorescent molecule and can bind to the second target; (p) operating the first bidirectional fluidic channel control unit so that the fluid mixed in step (o) flows from the mixing chamber into the purification chamber; (q) switching on the magnetic field generating unit so that the magnetic beads contained in the fluid in the purification chamber of step (p) are attracted onto the inner wall of the purification chamber; (r) operating the waste fluidic channel control unit so that the fluid in the purification chamber flows off via the waste fluidic channel; (s) loading a resuspension solution into the purification chamber and switching off the magnetic field generating unit so that the magnetic beads are resuspeneded in the resuspension solution; (t) operating the unidirectional fluidic channel control unit of another one of the at least two fluorescence detection units so that the resuspension solution flows from the purification chamber into the fluorescence detection area via the fluorescence detection fluidic channel; and (u) conducting fluorescence detections of the two fluorescence detection units to determine whether the sample contains the first and/or the second targets.

DETAILED DESCRIPTION OF THE PREFERRED EMBODIMENTS

Figure 1:
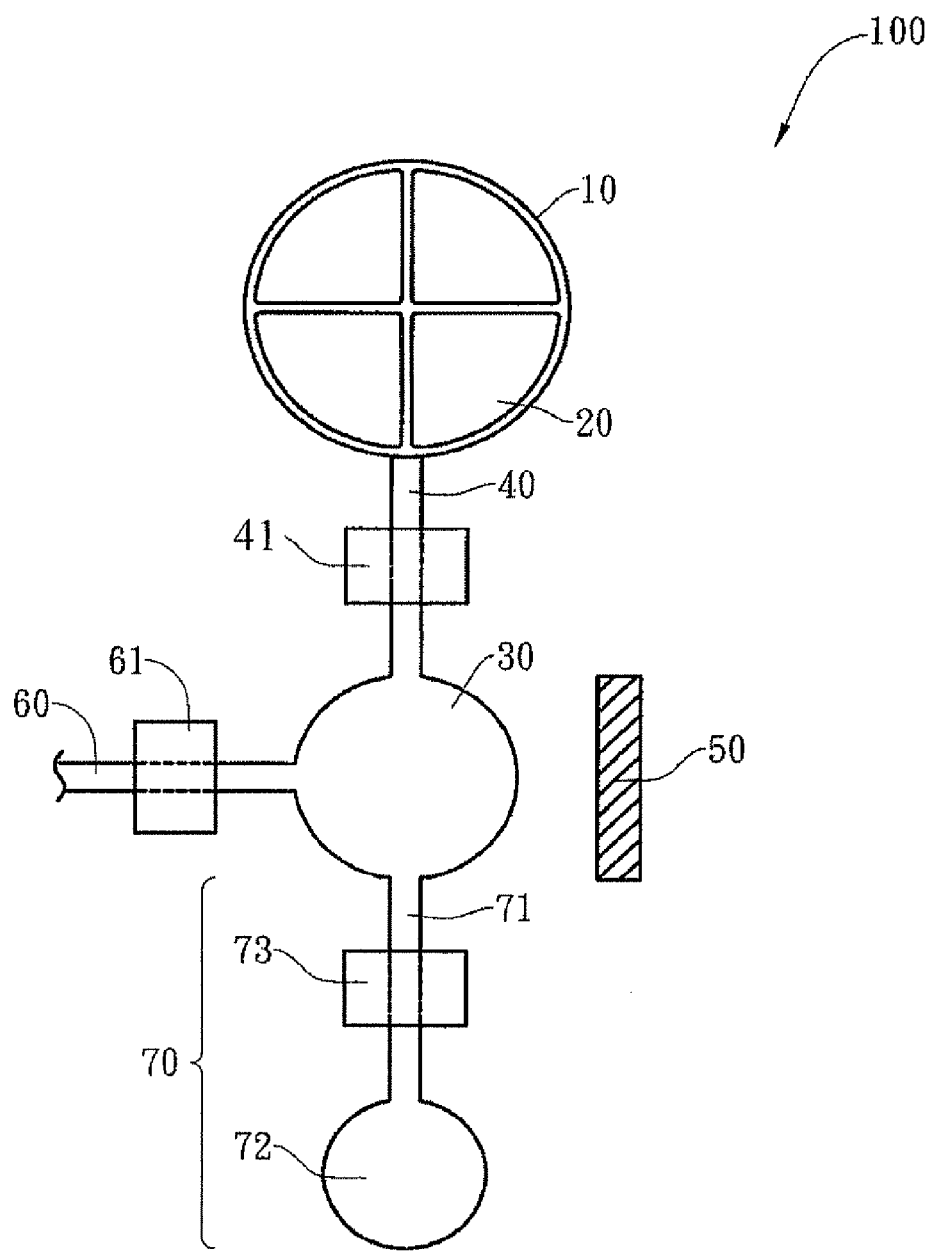
FIG. 1 shows an immunoassay biochip of the present invention having one fluorescence detection unit only.
Figure 2:
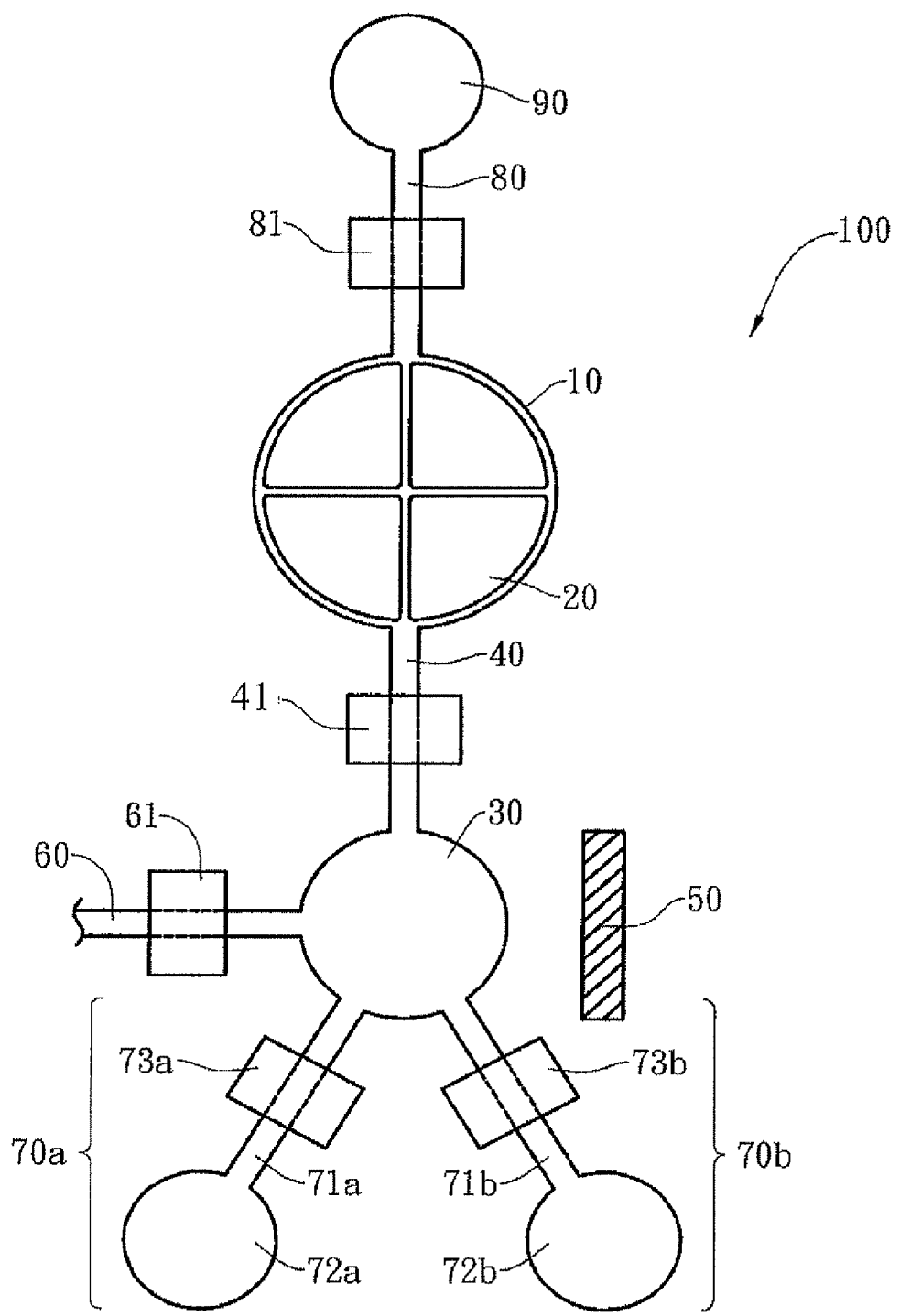
FIG. 2 shows an immunoassay biochip of the present invention having two fluorescence detection units.

FIG. 1 and FIG. 2 schematically show immunoassay biochips according to the present invention. Referring to FIG. 1, an immunoassay biochip 100 having one fluorescence detection unit 70 is shown. The biochip 100 comprises: a mixing chamber 10; a mixer 20 for mixing a fluid in the mixing chamber 10; a purification chamber 30; a first fluidic channel 40 for connecting the mixing chamber 10 and the purification chamber 30; a first bidirectional fluidic channel control unit 41 for controlling the flow directions of a fluid in the first fluidic channel 40; a magnetic field generating unit 50 for attracting magnetic matters in the purification chamber 30; a fluorescence detection unit 70, which comprises a fluorescence detection fluidic channel 71, a fluorescence detection area 72 and a unidirectional fluidic channel control unit 73, wherein the fluorescence detection fluidic channel 71 is used for connecting the purification chamber 30 and the fluorescence detection area 72, and the unidirectional fluidic channel control unit 73 is used for controlling the flow direction of a fluid in the fluorescence detection fluidic channel 71 so that the fluid flows from the purification chamber 30 into the fluorescence detection area 72; a waste fluidic channel 60 having one end connected to the purification chamber 30; and a waste fluidic channel control unit 61 for directing a waste fluid in the purification chamber 30 to flow off via the waste fluidic channel 60.

In the aforementioned biochip 100, the mixing chamber 10 is used for containing substances that are to be mixed later within the mixing chamber 10 by the mixer 20. A suitable shape for the mixing chamber 10 may include, but is not limited to, a cylinder.

In the aforementioned biochip 100, the mixer 20 is used for mixing fluids in the mixing chamber 10. In a preferred embodiment, the mixer 20 is formed by deformable membranes; with the membranes moving up and down, fluids in the mixing chamber 10 can be mixed. A suitable mixer 20 for the present invention may include, but is not limited to, a propeller-shaped membrane mixer 20.

Figure 3:
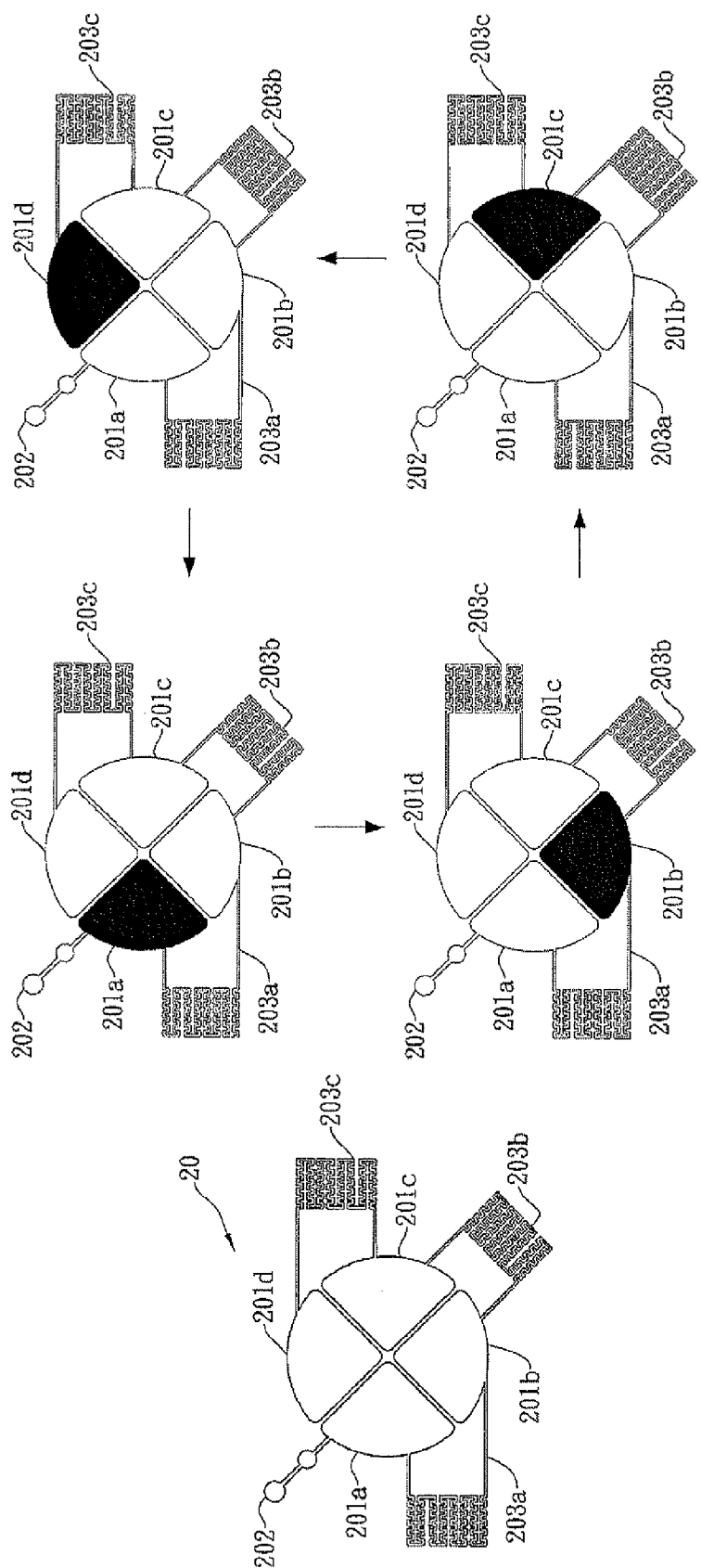
FIG. 3 shows propeller-shaped membrane mixer in an immunoassay biochip of the present invention.

The operation of the propeller-shaped membrane mixer 20 according to the present invention will be described with reference to FIG. 3. First, air is introduced into the mixer 20 via an air pore 202 and makes the first blade of the propeller-shaped membrane 201a inflate. Next, the air enters an air channel 203a and makes the second blade of the propeller-shaped membrane 201b inflate. Then, the air enters an air channel 203b and makes the third blade of the propeller-shaped membrane 201c inflate. Similarly, the air then enters an air channel 203c and makes the fourth blade of the propeller-shaped membrane 201d inflate. By repeating the above cycle, the membranes in the propeller-shaped membrane mixer 20 can inflate continuously and the fluids inside the mixing chamber 10 will be mixed.

In the aforementioned biochip 100, the mixing chamber 10 is connected to the purification chamber 30 which is having an inner wall. After a sample is properly mixed with magnetic matters in the mixing chamber 10, the magnetic matters can be attracted onto the inner wall of the purification chamber 30 by a magnetic field generated outside the purification chamber 30.

In the aforementioned biochip 100, the first fluidic channel 40 connects the mixing chamber 10 and the purification chamber 30, allowing fluids to flow inside.

In the aforementioned biochip 100, the first bidirectional fluidic channel control unit 41 controls the flow directions of a fluid in the first fluidic channel 40 and may be any means known in the art for controlling flow directions of a fluid. For example, it may be embodied by a configuration of one pump and two air pores.

Figure 5:
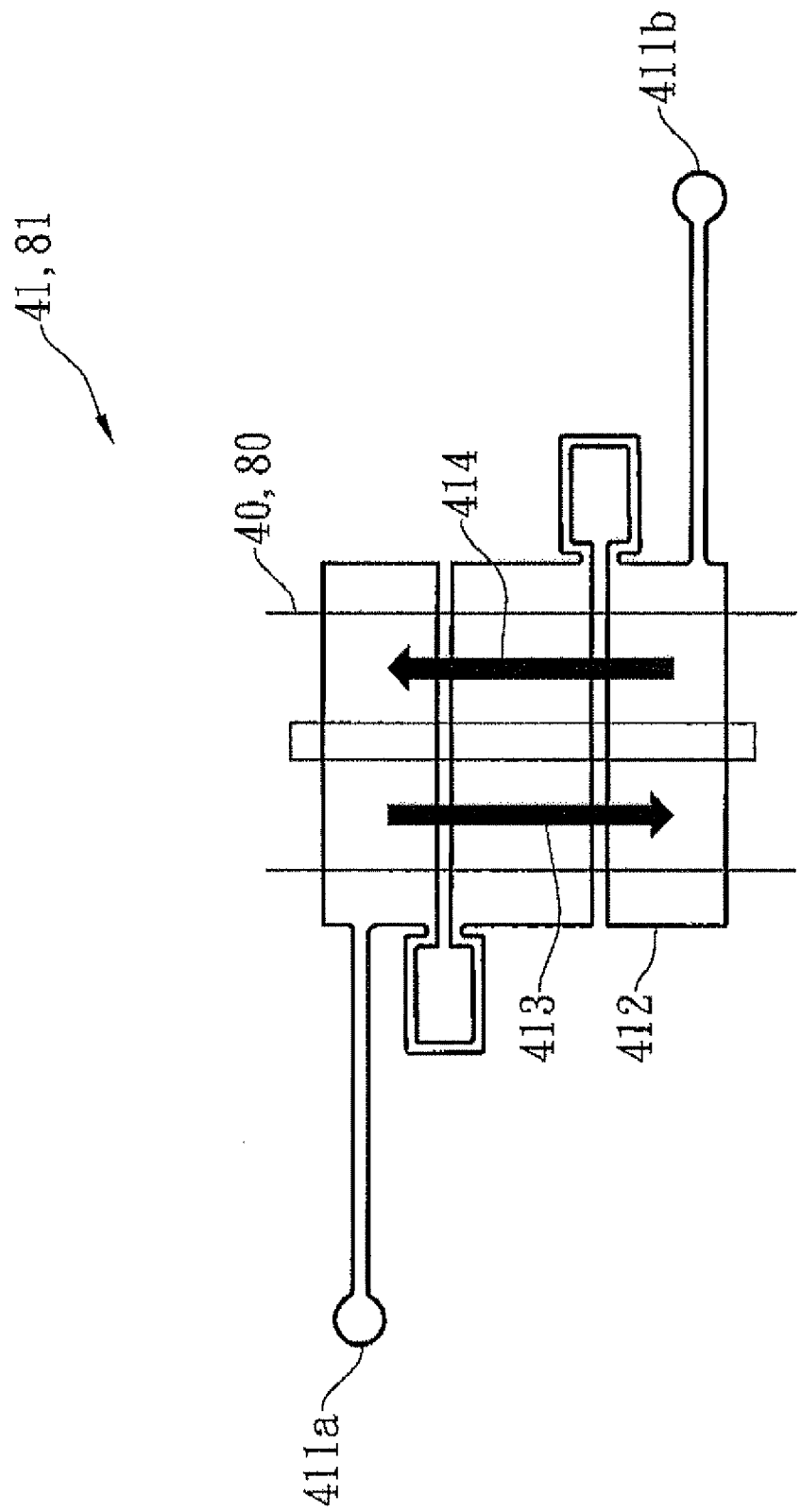
FIG. 5 shows a first bidirectional fluidic channel control unit in an immunoassay biochip of the present invention.

The operation of the first bidirectional fluidic channel control unit 41 according to the present invention will be described with reference to FIG. 5. When a user intends to make a fluid flow in the direction of arrow 413, air is first introduced into a pump 412 via an air pore 411a. Then, inside the pump 412, the air is forced to move from the end of the air pore 411a to the end of an air pore 411b; consequently, the fluid in the first fluidic channel will flow in the same direction, i.e., in the direction of arrow 413. It can be easily understood that when the user intends to make a fluid flow in the direction of arrow 414, air should be introduced into the pump 412 via the air pore 411b. The air inside the pump 412, then, is forced to move from the end of the air pore 411b to the end of the air pore 411a; consequently, the fluid in the first fluidic channel will flow in the same direction, i.e., in the direction of arrow 414.

The operation process of the second bidirectional fluidic channel control unit 81 according to the present invention is the same as that of the first bidirectional fluidic channel control unit 41 described above.

Figure 4:
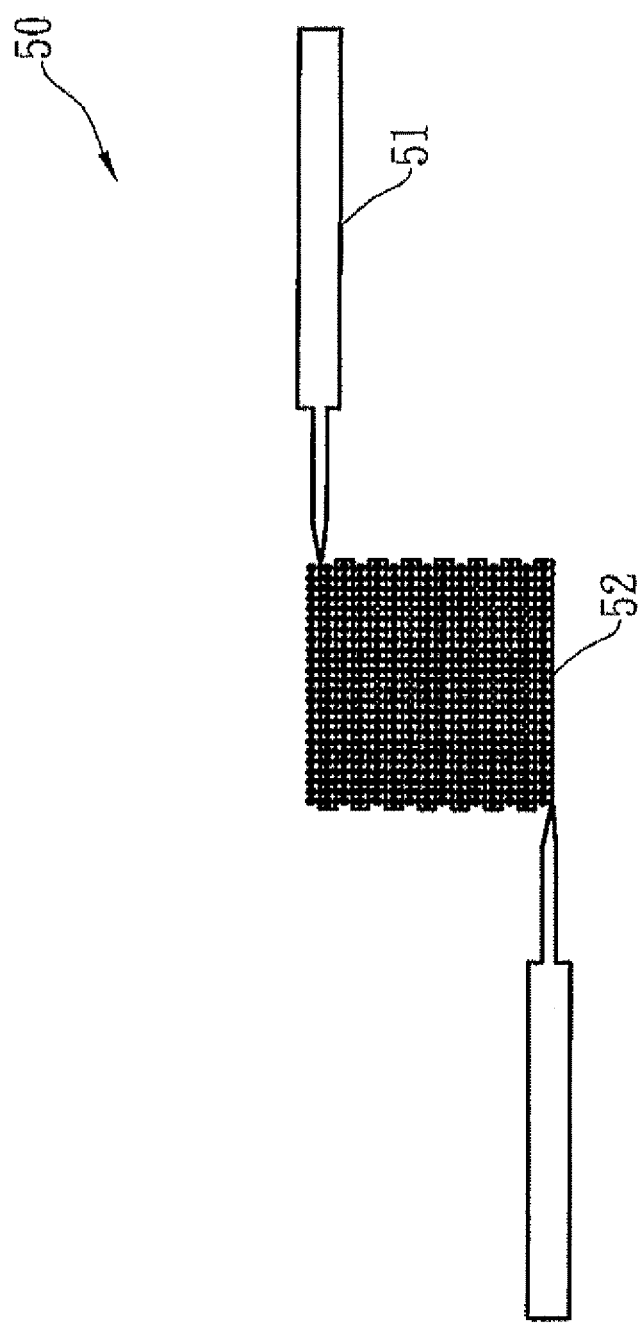
FIG. 4 shows a circular microcoils array in an immunoassay biochip of the present invention.

In the aforementioned biochip 100, the magnetic field generating unit 50 is used for generating a magnetic field inside the purification chamber 30; it may be located at positions as shown in FIGS. 1 and 2 (but the positions are not limited thereto). In either FIG. 1 or FIG. 2, the magnetic field generating unit 50 is located at one side of the purification chamber 30; magnetic matters inside the purification chamber 30 can thus be attracted onto the inner wall thereof due to the attraction of the magnetic field, thereby achieving the purification effect. It can be easily understood that the position where the magnetic field generating unit 50 is located as shown in FIGS. 1 and 2 may be adjusted depending on the position where a magnetic field is needed. For example, the magnetic field generating unit 50 may be located under the bottom of the purification chamber 30, so that the magnetic field is generated at the bottom of said chamber and that the magnetic matters are attracted onto the bottom of the purification chamber 30. A suitable magnetic field generating unit 50 may include, but is not limited to, a circular microcoils array 50 as shown in FIG. 4. A magnetic field can be generated by the microcoils 52 by directing a current to flow through terminals 51.

In the aforementioned biochip 100, the fluorescence detection unit 72 is used for detecting whether a sample contains fluorescent molecules. The fluorescence detection unit 73 comprises three elements: a fluorescence detection fluidic channel 71, a fluorescence detection area 72 and a unidirectional fluidic channel control unit 73. The fluorescence detection fluidic channel 71 connects the purification chamber 30 and the fluorescence detection area 72. The unidirectional fluidic channel control unit 73 controls the flow direction of a fluid in the fluorescence detection fluidic channel 71 and may be any means known in the art for causing fluids to flow in one direction. It can be easily understood that said unidirectional fluidic channel control unit 73 may be a bidirectional fluidic channel control unit as well, but it is used to control the fluid to flow in only one direction. The unidirectional fluidic channel control unit 73 may be embodied by a configuration of one pump and one air pore for example.

Figure 6:
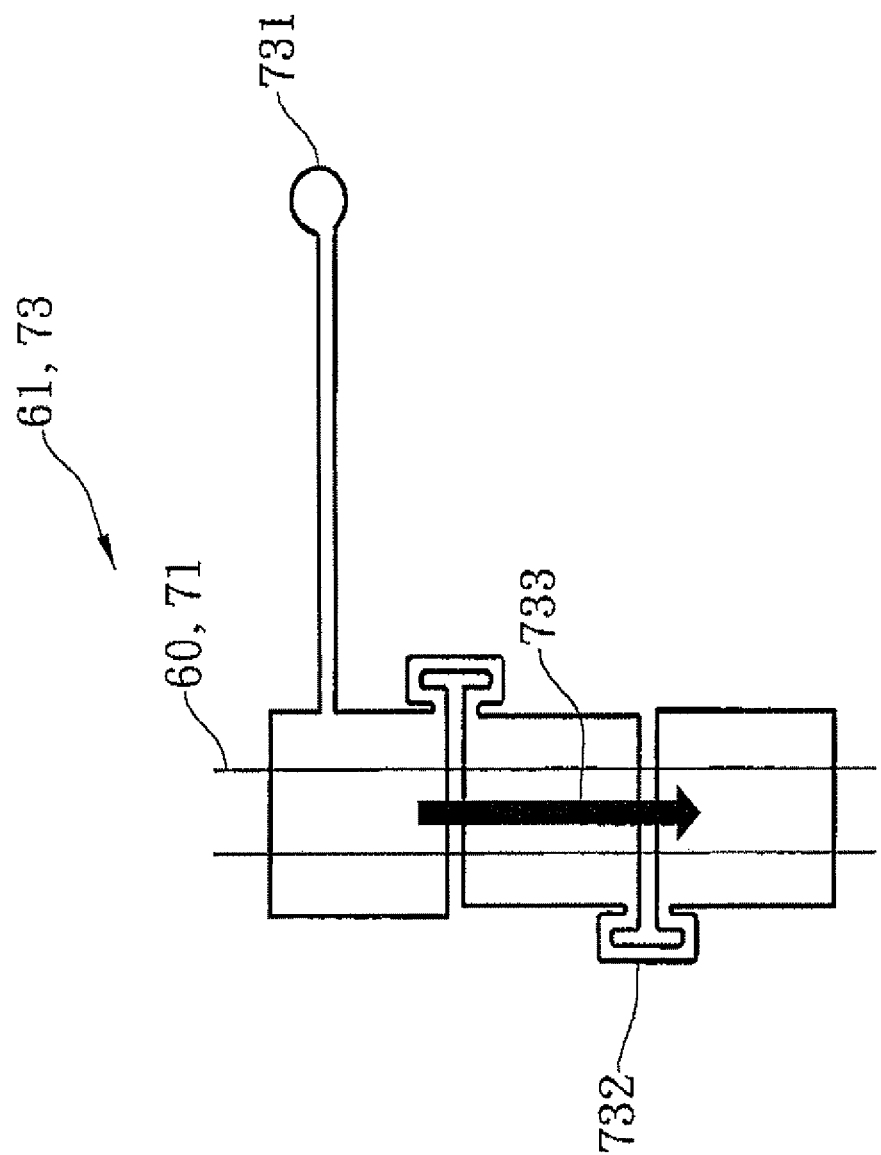
FIG. 6 shows a unidirectional fluidic channel control unit in an immunoassay biochip of the present invention.

The operation of the unidirectional fluidic channel control unit 73 according to the present invention will be described with reference to FIG. 6. First, air is introduced into a pump 732 via an air pore 731. The air is then forced to flow in the direction of arrow 733, and consequently, the fluid in the first fluidic channel will flow in the same direction, i.e., in the direction of arrow 733.

The operation process of the waste fluidic channel control unit 61 according to the present invention is the same as that of the unidirectional fluidic channel control unit 73 described above.

In the aforementioned biochip 100, the waste fluidic channel is provided to allow a waste fluid to flow off the biochip from the purification chamber 30. Generally, a waste fluidic channel 60 in a microfluidic biochip 100 may be connected to a collection chamber so that the waste fluid is collected for further processing.

In the aforementioned biochip 100, the waste fluidic channel control unit 61 directs a waste fluid in the purification chamber 30 to flow off via the waste fluidic channel 60 and may be embodied by a configuration of one pump and one air pore for example.

FIG. 2 shows an immunoassay biochip 100 according to another embodiment of the present invention. This embodiment is different from the first one in that the biochip 100 in the second embodiment has two fluorescence detection units 70a, 70b and a further storage chamber 90. Thus, the biochip 100 in FIG. 2 comprises a second fluidic channel 80 for connecting the mixing chamber 10 and the storage chamber 90, thereby allowing a fluid to flow in said second fluidic channel 80. Also, a second bidirectional fluidic channel control unit 81 is provided to control the flow directions of a fluid in the second fluidic channel 80. The second bidirectional fluidic channel control unit 81 may be any means known in the art for controlling flow directions of a fluid. For example, it may be embodied by, but is not limited to, a configuration of one pump and two air pores.

In FIG. 2, there are elements with the same reference numerals as in FIG. 1, and functions of those elements can be referred to the above descriptions.

A method of using the immunoassay biochip in FIG. 1 for determining whether a sample contains a target is described as follows: (a) First, load a sample to be tested and a solution containing magnetic beads into the mixing chamber 10 of the biochip 100 as shown in FIG. 1, and then operate the mixer 20 to mix the sample with the solution in the mixing chamber 10. Here, each of the magnetic beads is conjugated with a same type of capture antibody which can identify and capture a same type of target. If the sample contains said target such as a protein or an antigen, a magnetic bead will be able to capture the target. (b) Operate the first bidirectional fluidic channel control unit 41 so that the fluid mixed in step (a) flows into the purification chamber 30. (c) Switch on the magnetic field generating unit 50 to generate a magnetic field inside the purification chamber 30; the magnetic beads contained in the fluid in the purification chamber 30 are thus attracted onto the inner wall of the purification chamber 30. (d) Operate the waste fluidic channel control unit 61 so that the fluid in the purification chamber 30 of step (c) flows off via the waste fluidic channel 60. Here, the magnetic beads are still attracted by the magnetic field and will not flow off with the fluid. (e) Load a resuspension solution into the purification chamber 30 and then switch off the magnetic field generating unit 50 so that the magnetic beads are resuspended in the resuspension solution. (f) Operate the first bidirectional fluidic channel control unit 41 so that the resuspension solution flows into the mixing chamber 10 via the first fluidic channel 40. (g) Load a solution containing a same type of fluorescent antibodies into the mixing chamber 10 and then operate the mixer 20 to mix the solution with the resuspenstion solution in the mixing chamber 10. Here, each of the fluorescent antibodies has been labeled with a fluorescent molecule and is capable of identifying and binding to the target; thus, in this step, if a fluorescent antibody binds to the target, a bound form of magnetic bead-capture antibody-target-fluorescent antibody complex will be formed. (h) Operate the first bidirectional fluidic channel control unit 41 so that the fluid mixed in step (g) flows from the mixing chamber 20 into the purification chamber 30. (i) Switch on the magnetic field generating unit 50 so that the magnetic beads contained in the fluid in the purification chamber 30 of step (h) are attracted onto the inner wall of the purification chamber 30. Here, the excess fluorescent antibodies which did not bind to the targets remain in the fluid. (j) Operate the waste fluidic channel control unit 61 so that the fluid containing excess fluorescent antibodies which have not bound to the targets in the purification chamber 30 flows off via the waste fluidic channel 60. (k) Load a resuspension solution into the purification chamber 30 and then switch off the magnetic field generating unit 50 so that the magnetic beads are resuspended in the resuspension solution. (l) Operate the unidirectional fluidic channel control unit 73 of the fluorescence detection unit 70 so that the resuspension solution flows from the purification chamber 30 into the fluorescence detection area 72 via the fluorescence detection fluidic channel 71. (m) Finally, conduct a fluorescence detection to detect the fluorescence signals within the fluorescence detection area 72; the result concerning whether the sample contains any target and how many targets are contained in the sample can thus be determined.

In the aforementioned method, the capture antibody is a specific antibody used for identifying a target disease and is conjugated with a magnetic bead.

In the aforementioned method, the target is a specific antigen relevant to a particular disease, or a bound form of antigen-antibody complex which has already bound to an autoantibody.

For the embodiments where the target is an antigen, since the antigen includes a region having specificity for binding to the capture antibody and another region having specificity for binding to the fluorescent antibody, the target can bind respectively to the capture antibody as well as the fluorescent antibody without influencing one another. That is, after the capture antibody-binding region of the target binds to the capture body, the fluorescent antibody-binding region of the target can still bind to the fluorescent antibody. Likewise, after the fluorescent-antibody-binding region of the target binds to the fluorescent antibody, the capture antibody-binding region of the target can still bind to the capture antibody.

For the embodiments where the target is a bound form of antigen-antibody complex, since the antigen of the bound complex has specificity for binding to the capture antibody and the antibody of the bound complex has specificity for binding the fluorescent antibody, the target can bind respectively to the capture antibody as well as the fluorescent antibody without influencing one another. After the antigen of the bound complex binds to the capture body, the antibody the bound complex can still bind to the fluorescent antibody.

In the aforementioned method, the fluorescent antibody is used for identifying a target and is labeled with a fluorescent molecule that can be detected by the fluorescence detection unit. When the target is an antigen, the fluorescent antibody can identify it. Moreover, the binding site of the antigen and the fluorescent antibody is different from the binding site of the antigen and the capture antibody, and thus, the fluorescent antibody can still bind to the antigen which has already bound to the capture antibody. When the target is a bound form of the antigen-antibody complex, the fluorescent antibody can identify the antibody of the bound complex. The fluorescence detection unit can detect either of the fluorescent antibodies descried above.

In the aforementioned method, the resuspension solution is used for resuspending magnetic bead-binding complexes. The resuspension solution is prepared according to the properties of the magnetic beads, antibodies and antigens used in the assay. There is no specific limitation to the composition, pH, density or temperature of the resuspension solution, as long as these factors do not eliminate the activity of the magnetic beads, antibodies or antigens. An example of the resuspension solution is PBS (phosphate buffered saline).

A method of using the immunoassay biochip in FIG. 2 for determining whether a sample contains targets is described as follows: (a) First, load a sample to be tested and a solution containing magnetic beads into the mixing chamber 10 of the biochip 100 as shown in FIG. 2, and then operate the mixer 20 to mix the sample with the solution in the mixing chamber 10. Here, each of the magnetic beads is conjugated with a capture antibody which can identify and capture either a first target or a second target. (b) Operate the first bidirectional fluidic channel control unit 41 so that the fluid mixed in step (a) flows into the purification chamber 30. (c) Switch on the magnetic field generating unit 50 so that the magnetic beads contained in the fluid in the purification chamber 30 of step (b) are attracted onto the inner wall of the purification chamber 30. (d) Operate the waste fluidic channel control unit 61 so that the fluid in the purification chamber 30 of step (c) flows off via the waste fluidic channel 60. (e) Load a resuspension solution into the purification chamber 30 and then switch off the magnetic field generating unit 50 so that the magnetic beads are resuspended in the resuspension solution. (f) Operate the first bidirectional fluidic channel control unit 41 so that the resuspension solution flows into the mixing chamber 10 via the first fluidic channel 40. (g) Operate the second bidirectional fluidic channel control unit 81 so that part of the fluid in the mixing chamber 10 flows into the storage chamber 90. (h) Load a solution containing first fluorescent antibodies into the mixing chamber 10 and then operate the mixer 20 to mix the solution with the fluid in the mixing chamber 10. Here, each of the first fluorescent antibodies has been labeled with a fluorescent molecule and is capable of identifying and binding to a first target; thus, in this step, if a first fluorescent antibody binds to the first target, a bound form of magnetic bead-capture antibody-first target-first fluorescent antibody complex will be formed. (i) Operate the first bidirectional fluidic channel control unit 41 so that the fluid mixed in step (h) flows from the mixing chamber 10 into the purification chamber 30. (j) Switch on the magnetic field generating unit 50 so that the magnetic beads contained in the fluid in the purification chamber 30 of step (i) are attracted onto the inner wall of the purification chamber 30. Here, the excess first fluorescent antibodies which did not bind to the targets remain in the fluid in the purification chamber 30. (k) Operate the waste fluidic channel control unit 61 so that the fluid in the purification chamber 30 flows off via the waste fluidic channel 60. (l) Load a resuspension solution into the purification chamber 30 and then switch off the magnetic field generating unit 50 so that the magnetic beads are resuspended in the resuspension solution. (m) Operate the unidirectional fluidic channel control unit 73a of the fluorescence detection unit 70a so that the resuspension solution flows from the purification chamber 30 into the fluorescence detection area 72a via the fluorescence detection fluidic channel 71a. (n) Operate the second bidirectional fluidic channel control unit 81 so that the fluid in the storage chamber 90 of step (g) flows from the storage chamber 90 into the mixing chamber 10. (o) Load a solution containing second fluorescent antibodies into the mixing chamber 10 and then operate the mixer 20 to mix the solution with the fluid in the mixing chamber 10. Here, each of the second fluorescent antibodies has been labeled with a fluorescent molecule and is capable of identifying and binding to a second target. (p) Operate the first bidirectional fluidic channel control unit 41 so that the fluid mixed in step (o) flows from the mixing chamber 10 into the purification chamber 30. (q) Switch on the magnetic field generating unit 50 so that the magnetic beads contained in the fluid in the purification chamber 30 of step (p) are attracted onto the inner wall of the purification chamber 30. (r) Operate the waste fluidic channel control unit 61 so that the fluid in the purification chamber 30 flows off via the waste fluidic channel 60. (s) Load a resuspension solution into the purification chamber 30 and then switch off the magnetic field generating unit 50 so that the magnetic beads are resuspended in the resuspension solution. (t) Operate the unidirectional fluidic channel control unit 73b of the fluorescence detection unit 70b so that the resuspension solution flows from the purification chamber 30 into the fluorescence detection area 72b via the fluorescence detection fluidic channel 71b. (u) Conduct fluorescence detections to detect the fluorescence signals within the fluorescence detection areas 72a and 72b; whether the sample contains the first and/or the second targets can thus be determined.

In the aforementioned method, the capture antibody is a specific antibody that can identify a particular biomarker molecule for a target disease. The first target and the second target are different bound forms of the antigen-antibody complex having identical antigens but different antibodies, wherein the antigens can be identified by the capture antibodies.

In the aforementioned method, since the antigen portion of the first target has specificity for binding to the capture antibody and the antibody portion of the first target has specificity for binding to the first fluorescent antibody, the first target can bind respectively to the capture antibody as well as the first fluorescent antibody without influencing one another. That is, after the antigen portion of the first target binds to the capture body, the antibody portion of the first target can still bind to the first fluorescent antibody.

In the aforementioned method, since the antigen portion of the second target has specificity for binding to the capture antibody and the antibody portion of the second target has specificity for binding to the second fluorescent antibody, the second target can bind respectively to the capture antibody as well as the second fluorescent antibody without influencing one another. That is, after the antigen portion of the second target binds to the capture antibody, the antibody portion of the second target can still bind to the second fluorescent antibody.

It can be easily understood that when referring to the elements illustrated in FIGS. 1 and 2 to figure out the above methods of using an immunoassay biochip, if two elements have the same titles and reference numerals, they perform substantially the same function.

In the aforementioned method of using an immunoassay biochip as shown in FIG. 2, the first fluorescent antibody is used for identifying a first target and is labeled with a fluorescent molecule that can be detected by the fluorescence detection unit. The first fluorescent antibody is capable of identifying the antibody portion of the first target, which is a bound antigen-antibody complex.

In the aforementioned method, the second fluorescent antibody is used for identifying a second target and is labeled with a fluorescent molecule that can be detected by the fluorescence detection unit. The second fluorescent antibody is capable of identifying the antibody portion of the second target, which is a bound antigen-antibody complex.

In the aforementioned method, the fluorescent molecules labeled to the first and second fluorescent antibodies may be of the same or different types for the purpose of identifying different immunoglobulin antibodies. After the targets are identified respectively by the first and second fluorescent antibodies and then bind to the magnetic beads, the fluid containing the first targets will flow to the first fluorescence detection unit while the fluid containing the second targets to the second fluorescence detection unit. Thereafter, fluorescence detections can be conducted, so that the result of whether the sample contains the first and/or second targets is acquired at the same time.

Several embodiments of the present invention will be described below, which are used to further illustrate the advantages rather than limit the scope of claims of the present invention.

EXAMPLE 1

Using an Immunoassay Biochip of the Present Invention in Dengue Virus Assay

The operation of the immunoassay biochip in this embodiment will be described with reference to FIG. 2. First, dengue viruses (DV serotype I-IV) and 4.5 μm micro-magnetic beads conjugated with anti-DV antibodies are introduced into the mixing chamber 10 of the biochip. Then, the membrane-formed mixer 20 is turned on. Driven by the mixer 20, the membranes at the bottom of the mixing chamber 10 will repeat up-and-down movements, thereby mixing the magnetic beads and the dengue viruses completely. Due to the affinity interaction of the antibody-antigen, the dengue viruses are then bound to the anti-DV antibodies which are conjugated with the magnetic beads. Next, the mixed fluid is transported to the magnetic beads purification chamber 30. A circular microcoils array 50 is provided near the bottom of the purification chamber 30; thus, after an electric current flows through the microcoils, a micro-magnetic field is generated, which attracts the magnetic beads bound with dengue viruses onto the inner wall surface of the purification chamber 30. Then, 1×PBS (phosphate buffered saline) is introduced into the purification chamber 30 via the first bidirectional fluidic channel control unit 41, and the residual dengue viruses which did not bond to the magnetic beads are washed away and transported to the waste fluidic channel 60. Then close the electric current. Thereafter, a clinical sample (such as a serum sample) is introduced into the mixing chamber 10, and the purified magnetic beads are also transported to the mixing chamber 10 via the first bidirectional fluidic channel control unit 41. Again, the propeller-shaped membrane mixer 20 is turned on to mix the serum sample and the magnetic beads bound with dengue viruses completely in the mixing chamber 10. Due to the affinity interaction of the antibody-antigen, the anti-DV antibodies in the serum sample will bind to the magnetic beads which are conjugated with the dengue viruses. Thereafter, the mixed fluid is transported to the magnetic beads purification chamber 30. Similarly, after an electric current flows through the microcoils array 50, a micro-magnetic field is generated to attract the magnetic beads onto the inner wall surface of the purification chamber 30, wherein the magnetic beads are bound with the anti-DV antibodies which were contained in the serum sample. Then, 1×PBS is introduced into the purification chamber 30 via the bidirectional first bidirectional fluidic channel control unit 41, and the residual substances which did not bond to the magnetic beads are washed away and transported to the waste fluidic channel 60. Then close the electric current. After purification, all of the magnetic beads are transported to the mixing chamber 10 via the first bidirectional fluidic channel control unit 41. Then, half of the magnetic beads are transported to a temporary storage area (the storage chamber 90) via the bidirectional fluidic channel pump 81. Next, fluorescent detection antibodies of a first type (donkey anti-human IgM-PE) are introduced into the mixing chamber 10 and then mixed completely with the magnetic beads by the work of the membrane-formed mixer 20; the mixed fluid is transported to the magnetic beads purification chamber 30. Similarly, after a current is directed through the microcoils array 50, a micro-magnetic field is generated to attract the magnetic beads onto the inner wall surface of the purification chamber 30, wherein the magnetic beads are bound with the detection antibodies. Then, PBS is introduced into the purification chamber 30 via the first bidirectional fluidic channel control unit 41, and the residual detection antibodies which did not bond to the magnetic beads are washed away and transported to the waste fluidic channel 60. Thereafter, PBS is introduced again into the purification chamber 30 to a certain volume, and the current going through the microcoils array 50 is stopped so that the magnetic beads are resuspended in the PBS. Then, the unidirectional fluidic channel pump 73a is turned on to transport the fluid from the purification chamber 30 into the fluorescence detection area 72a. Next, the magnetic beads stored in the temporary storage area 90 are transported to the mixing chamber 10, and fluorescent detection antibodies of another type (goat anti-human IgG-FITC) are also introduced into the mixing chamber 10. By the work of the membrane-formed mixer 20; the fluorescent detection antibodies and the magnetic beads are completely mixed and then transported to the magnetic beads purification chamber 30. Similarly, a current is directed through the microcoils array 50 and a micro-magnetic field is generated to attract the magnetic beads onto the inner wall surface of the purification chamber 30, wherein the magnetic beads are bound with detection antibodies of the second type. Then, PBS is introduced into the purification chamber 30 via the first bidirectional fluidic channel control unit 41 to wash away the residual detection antibodies which did not bond to the magnetic beads and which are later transported to the waste fluidic channel 60. Thereafter, PBS is introduced again into the purification chamber 30 to a certain volume, and the current going through the microcoils array 50 is stopped so that the magnetic beads are resuspended in the PBS. Then, the unidirectional fluidic channel control unit 73b is turned on to transport the fluid from the purification chamber 30 into the fluorescence detection area 72b. Finally, fluorescence detections can be conducted within the fluorescence detection areas 72a and 72b.

EXAMPLE 2

Figure 7A:
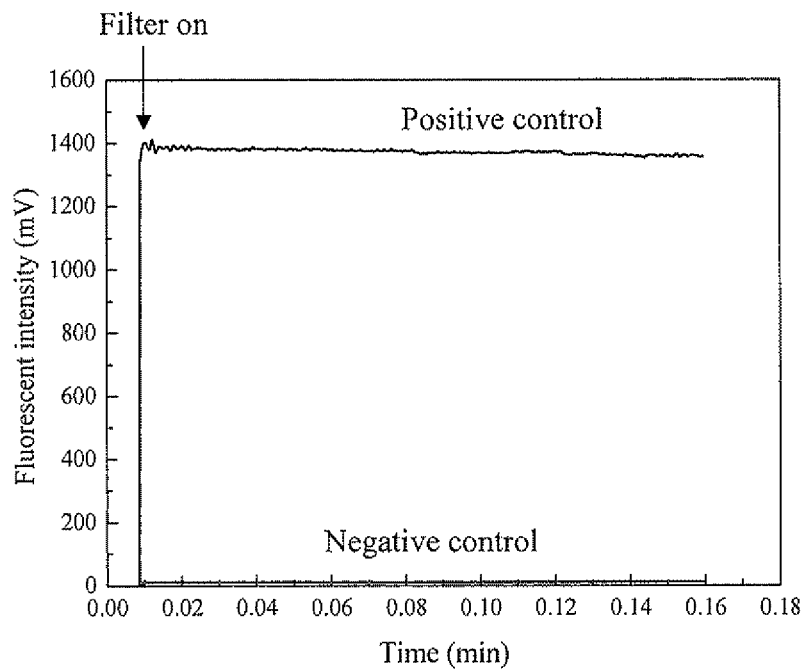
FIG. 7 shows the experiment result of determining the minimum concentration of antibodies required in an assay using an immunoassay biochip of the present invention.
Figure 7B:
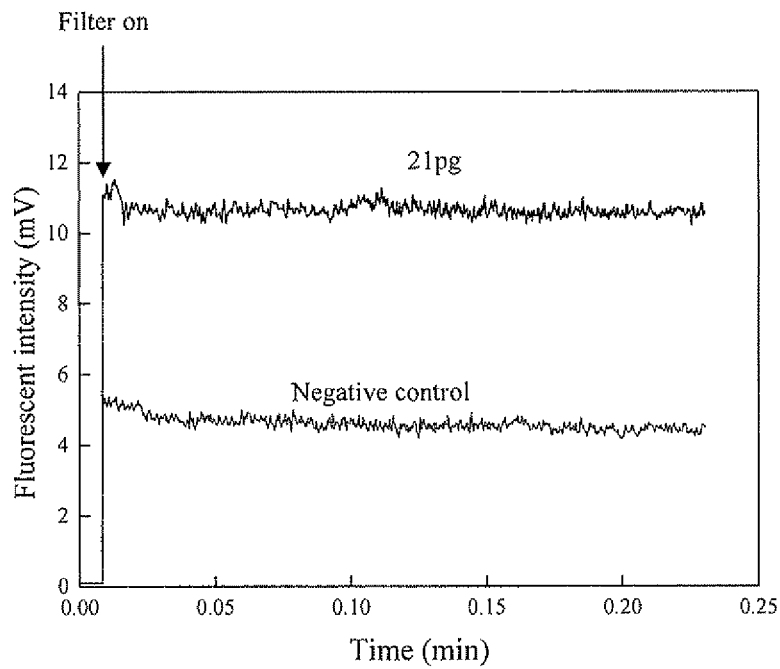

Determining the Minimum Concentration of Antibodies Required in an Assay Using an Immunoassay Biochip of the Present Invention FIGS. 7A and 7B show the experiment results with respect to determining the minimum concentration of antibodies. The experiment begins by conjugating 5 μl of magnetic beads which have been bound with anti-DV antibodies, with 100 μl of dengue viruses. Then, secondary antibodies with a known concentration are diluted to eight different concentrations: 45 ng, 22.5 ng, 11.25 ng, 5.625 ng, 1.406 ng, $8.76 \times 10^{-2}$ ng, $2.19\times10^{-2}$ ng, and $1.09\times10^{-2}$ ng. Next, 100 μl of the diluted secondary antibodies of each concentration are introduced, and then mixed with the above magnetic complexes. Finally, a fluorescence detection system is used to detect the fluorescence signals, and the minimum concentration of the antibodies required in an assay using the present immunoassay biochip can thus be determined.

In FIG. 7A, the horizontal axis represents time measured in minutes, and the vertical axis represents detected fluorescence intensities. The positive control shown in FIG. 7A uses secondary fluorescent antibodies of the highest concentration (45 ng) to bond to magnetic beads which have been bound with primary antibodies and dengue viruses. In contrast, the negative control uses the same secondary fluorescent antibodies (45 ng) to bond to magnetic beads which have been conjugated with primary antibodies only; since said magnetic beads are free from any dengue viruses, the secondary fluorescent antibodies cannot bond to said magnetic beads. Thus, the detected fluorescence intensities of the negative control are quite low.

Similarly in FIG. 7B, the horizontal axis represents time measured in minutes, and the vertical axis represents detected fluorescence intensities. The results marked with 21 pg show the fluorescence intensities detected when secondary fluorescent antibodies with a concentration of $2.19\times10^{-2}$ ng (21 pg) are used; in FIG. 7B, said detection results are compared with those of the negative control depicted in FIG. 7a. In this experiment, fluorescence detections are conducted toward the antibody samples of eight different concentrations (as described above); then, the s/n ratio of each sample is also obtained and compared with the result of the negative control, wherein the s/n ratio shall be greater than 3 to be an effective value. The experiment result shows that the s/n ratio of the antibody sample at a concentration of $2.19\times10^{-2}$ ng is 4.02, and the s/n ratio at a concentration of $1.09\times10^{-2}$ ng is 1.57. Therefore, the minimum concentration of antibodies required for the present immunoassay biochip is 21 pg.

EXAMPLE 3

Figure 8:
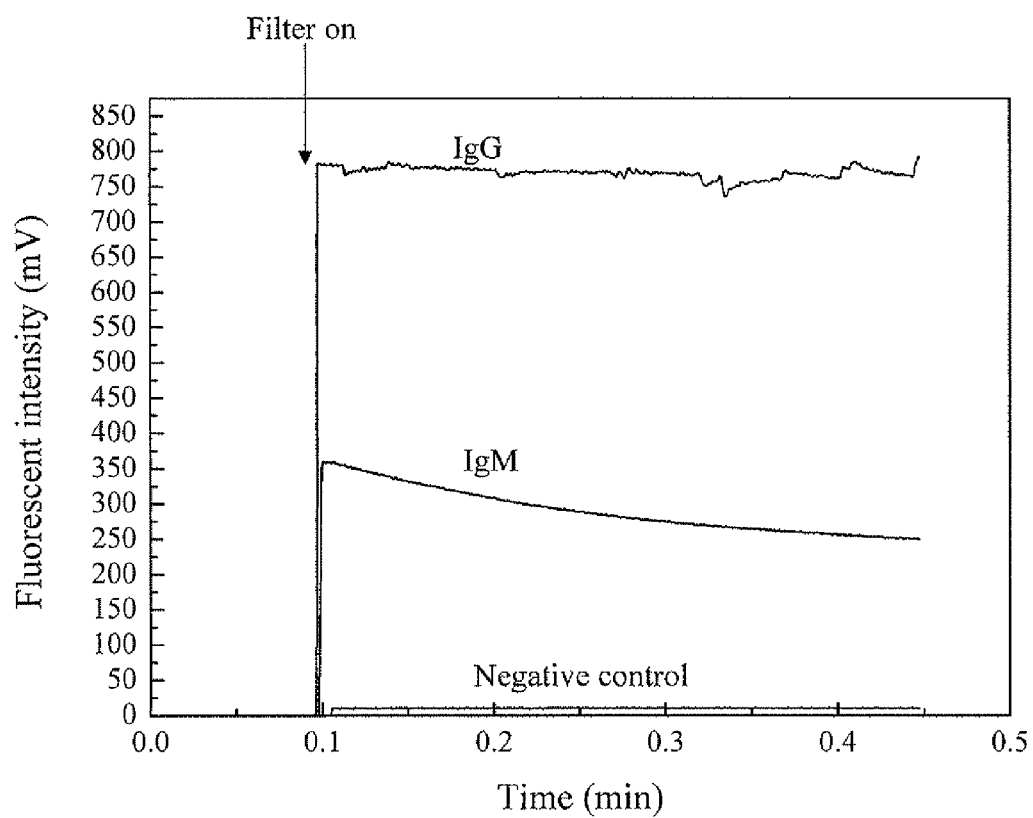
FIG. 8 shows the fluorescence signals of IgG and IgM in a serum sample assayed by an immunoassay biochip of the present invention.

The Concentrations of IgG and IgM in a Serum Sample Assayed by an Immunoassay Biochip of the Present Invention 5 μl of magnetic beads conjugated with anti-DV antibodies are mixed with 100 μl of dengue viruses in the immunoassay biochip of the present invention, and then 100 μl of a dengue-fever patient's serum sample is introduced. After the purification of the mixed fluid, two types of secondary fluorescent antibodies, 100 μl of goat antihuman IgG-FITC and 100 μl of donkey anti-human IgM-PE, are introduced into the present biochip respectively. Then, the present biochip is used to detect the fluorescence signals. The detection results are shown in FIG. 8, in which the horizontal axis represents time measured in minutes and the vertical axis represents fluorescence intensities. The negative control is a sample containing no serums, and the result shows no fluorescence signals are detected in said sample. And the detected fluorescence intensities of IgG and IgM are as shown in FIG. 8.

EXAMPLE 4

Figure 9:
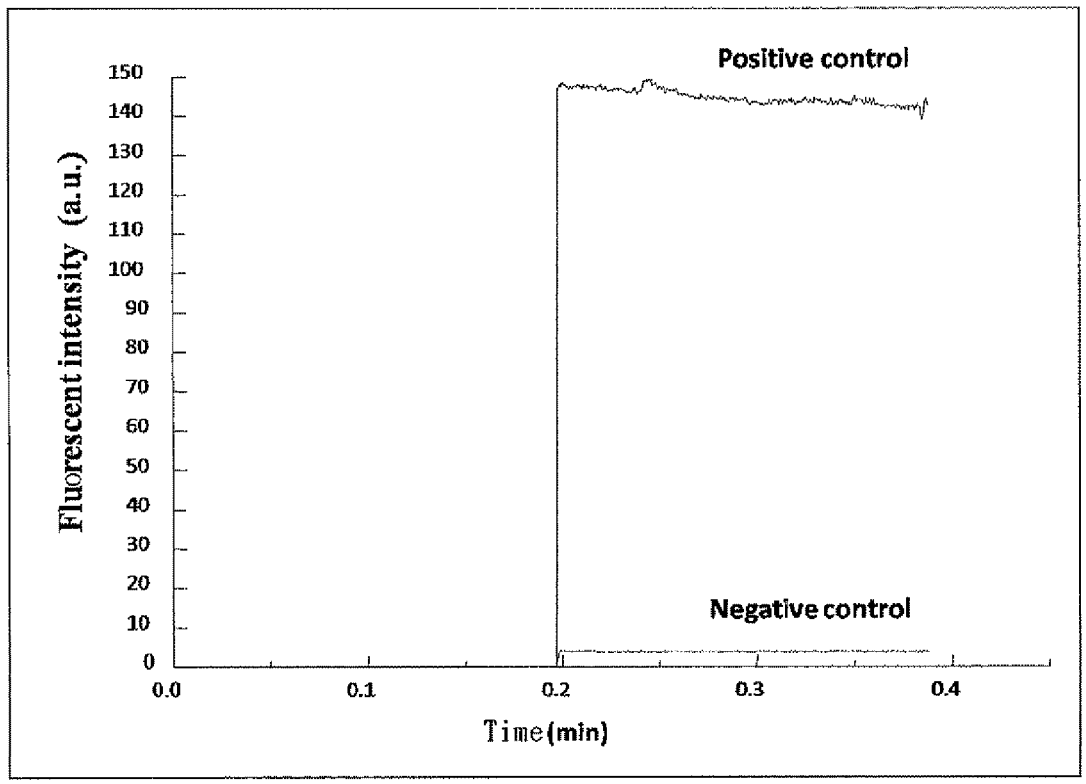
FIG. 9 show the experiment result of using an immunoassay biochip of the present invention for virus detection.

Using an Immunoassay Biochip of the Present Invention for Dengue Virus Detection 100 μl ($10^6$ pfu/ml) of a sample containing dengue viruses is introduced to be mixed with 5 μl of magnetic beads which have been bound with anti-DV antibodies. Next, 100 μl of fluorescent antibodies are introduced and mixed with the above fluid completely. The fluorescence detection unit is then used to detect fluorescence signals of the mixed fluid, so that presence of the viruses (i.e., antigens) can be affirmed. FIG. 9 shows the detection results of this experiment; the horizontal axis represents time measured in minutes, and the vertical axis represents detected fluorescence intensities. The results of the negative control show the detected fluorescence signals of a sample free from any viruses, and the results of the positive control show the signals of the sample containing magnetic beads bound with anti-DV antibodies.

In sum, with an immunoassay biochip of the present invention, both IgG and IgM in a sample can be detected simultaneously within 30 minutes; thus, whether a patient is having an acute or chronic infection can be determined in a short time. Moreover, unlike a conventional ELISA assay which only involves a two-dimensional detection, an assay method according to the present invention uses magnetic beads which, with the three-dimensional structures, improve the bonding abilities between the assay tool and antigen/antibodies by 10 to 50 times. An immunoassay biochip of the present invention is successfully integrated and miniaturized; thus, it is a portable device that allows a user to do a dengue infection assay at any time. Also, this microfluidic device serves as an integrated platform where biological samples can be transported and mixed automatically, thereby minimizing instabilities resulted from manual operations. An immunoassay biochip of the present invention has a size of 37 mm×53 mm. Other than the advantages of detecting two immunoglobulins simultaneously, portability of the device and lowered fabrication cost, the present biochip, with its feature of automatic operations, is also beneficial for reducing sample extraction time and increasing assay accuracy.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

The preferred embodiments of the present invention have been disclosed in the examples. However the examples should not be construed as a limitation on the actual applicable scope of the invention, and as such, all modifications and alterations without departing from the spirits of the invention and appended claims, including the other embodiments shall remain within the protected scope and claims of the invention.

What is claimed is:
1. An immunoassay biochip, which comprises:
   a mixing chamber;
   a mixer for mixing a fluid in the mixing chamber, comprising: a plurality of deformable propeller-shaped membranes, an air pore and a plurality of air channels, wherein the deformable propeller-shaped membranes are installed at the bottom of the mixing chamber and connected to the air pore and air channels;
   a purification chamber;
   a first fluidic channel for connecting the mixing chamber and the purification chamber;
   a first bidirectional fluidic channel control unit for controlling the flow directions of a fluid in the first fluidic channel;

a magnetic field generating unit for attracting magnetic matters in the purification chamber;

a fluorescence detection unit, which comprises a fluorescence detection fluidic channel, a fluorescence detection area and a unidirectional fluidic channel control unit, wherein the fluorescence detection fluidic channel is used for connecting the purification chamber and the fluorescence detection area, and the unidirectional fluidic channel control unit is used for controlling the flow direction of a fluid in the fluorescence detection fluidic channel so that the fluid flows from the purification chamber into the fluorescence detection area;

a waste fluidic channel having one end connected to the purification chamber; and a waste fluidic channel control unit for directing a waste fluid in the purification chamber to flow off via the waste fluidic channel.

2. The biochip of claim 1, wherein the first bidirectional fluidic channel control unit comprises two air pores and a pump.

3. The biochip of claim 1, wherein the unidirectional fluidic channel control unit comprises an air pore and a pump.

4. The biochip of claim 1, wherein the magnetic field generating unit is a circular microcoils array.

5. The biochip of claim 1, wherein the waste fluidic channel control unit comprises an air pore and a pump.

6. An immunoassay biochip, which comprises:
a mixing chamber;
a mixer for mixing a fluid in the mixing chamber, comprising: a plurality of deformable propeller-shaped membranes, an air pore and a plurality of air channels, wherein the deformable propeller-shaped membranes are installed at the bottom of the mixing chamber and connected to the air pore and air channels;
a purification chamber;
a first fluidic channel for connecting the mixing chamber and the purification chamber;
a first bidirectional fluidic channel control unit for controlling the flow directions of a fluid in the first fluidic channel;
a magnetic field generating unit for attracting magnetic matters in the purification chamber;
a storage chamber;
a second fluidic channel for connecting the mixing chamber and the storage chamber;
a second bidirectional fluidic channel control unit for controlling the flow directions of a fluid in the second fluidic channel;
at least two fluorescence detection units, which respectively comprises a fluorescence detection fluidic channel, a fluorescence detection area and a unidirectional fluidic channel control unit, wherein the fluorescence detection fluidic channel is used for connecting the purification chamber and the fluorescence detection area, and the unidirectional fluidic channel control unit is used for controlling the flow direction of a fluid in the fluorescence detection fluidic channel so that the fluid flows from the purification chamber into the fluorescence detection area;
a waste fluidic channel having one end connected to the purification chamber; and
a waste fluidic channel control unit for directing a waste fluid in the purification chamber to flow off via the waste fluidic channel.

7. The biochip of claim 6, wherein each of the first bidirectional fluidic channel control unit and the second bidirectional fluidic channel control unit comprises two air pores and a pump.

8. The biochip of claim 6, wherein the unidirectional fluidic channel control unit comprises an air pore and a pump.

9. The biochip of claim 6, wherein the magnetic field generating unit is a circular microcoils array.

10. The biochip of claim 6, wherein the waste fluidic channel control unit comprises an air pore and a pump.

11. A method of using the biochip of claim 1 for determining whether a sample contains a target, including the steps of:
(a) loading a sample and a solution containing a magnetic bead into the mixing chamber and then operating the mixer to mix the sample with the solution in the mixing chamber, wherein the magnetic bead is conjugated with a capture antibody for identifying and capturing a target;
(b) operating the first bidirectional fluidic channel control unit so that the fluid mixed in step (a) flows into the purification chamber;
(c) switching on the magnetic field generating unit so that the magnetic bead contained in the fluid in the purification chamber of step (b) is attracted onto the inner wall of the purification chamber;
(d) operating the waste fluidic channel control unit so that the fluid in the purification chamber of step (c) flows off via the waste fluidic channel;
(e) loading a resuspension solution into the purification chamber and switching off the magnetic field generating unit so that the magnetic bead is resuspended in the resuspension solution;
(f) operating the first bidirectional fluidic channel control unit so that the resuspension solution flows into the mixing chamber via the first fluidic channel;
(g) loading a solution containing a fluorescent antibody into the mixing chamber and operating the mixer to mix the solution with the resuspension solution in the mixing chamber, wherein the fluorescent antibody is labeled with a fluorescent molecule and can bind to the target;
(h) operating the first bidirectional fluidic channel control unit so that the fluid mixed in step (g) flows from the mixing chamber into the purification chamber;
(i) switching on the magnetic field generating unit so that the magnetic bead contained in the fluid in the purification chamber of step (h) is attracted onto the inner wall of the purification chamber;
(j) operating the waste fluidic channel control unit so that the fluid in the purification chamber flows off via the waste fluidic channel;
(k) loading a resuspension solution into the purification chamber and switching off the magnetic field generating unit so that the magnetic bead is resuspended in the resuspension solution;
(l) operating the unidirectional fluidic channel control unit of the fluorescence detection unit so that the resuspension solution flows from the purification chamber into the fluorescence detection area via the fluorescence detection fluidic channel; and
(m) conducting a fluorescence detection to determine whether the sample contains a target.

12. The method of claim 11, wherein the target is a bound form of antigen-antibody complex.

13. The method of claim1 1, wherein the target is an antigen.

14. A method of using the biochip of claim 6 for determining whether a sample contains targets, including the steps of:

(a) loading a sample and a solution containing magnetic beads into the mixing chamber and then operating the mixer to mix the sample with the solution in the mixing chamber, wherein the magnetic beads are conjugated with capture antibodies for identifying and capturing a first target and a second target;

(b) operating the first bidirectional fluidic channel control unit so that the fluid mixed in step (a) flows into the purification chamber;

(c) switching on the magnetic field generating unit so that the magnetic beads contained in the fluid in the purification chamber of step (b) are attracted onto the inner wall of the purification chamber;

(d) operating the waste fluidic channel control unit so that the fluid in the purification chamber of step (c) flows off via the waste fluidic channel;

(e) loading a resuspension solution into the purification chamber and switching off the magnetic field generating unit so that the magnetic beads are resuspended in the resuspension solution;

(f) operating the first bidirectional fluidic channel control unit so that the resuspension solution flows into the mixing chamber via the first fluidic channel;

(g) operating the second bidirectional fluidic channel control unit so that part of the fluid in the mixing chamber flows into the storage chamber;

(h) loading a solution containing a first fluorescent antibody into the mixing chamber and operating the mixer to mix the solution with the fluid in the mixing chamber, wherein the first fluorescent antibody is labeled with a fluorescent molecule and can bind to the first target;

(i) operating the first bidirectional fluidic channel control unit so that the fluid mixed in step (h) flows from the mixing chamber into the purification chamber;

(j) switching on the magnetic field generating unit so that the magnetic beads contained in the fluid in the purification chamber of step (i) are attracted onto the inner wall of the purification chamber;

(k) operating the waste fluidic channel control unit so that the fluid in the purification chamber flows off via the waste fluidic channel;

(l) loading a resuspension solution into the purification chamber and switching off the magnetic field generating unit so that the magnetic beads are resuspended in the resuspension solution;

(m) operating the unidirectional fluidic channel control unit of one of the at least two fluorescence detection units so that the resuspension solution flows from the purification chamber into the fluorescence detection area via the fluorescence detection fluidic channel of the one of the at least two fluorescence detection units;

(n) operating the second bidirectional fluidic channel control unit so that the fluid in the storage chamber of step (g) flows from the storage chamber into the mixing chamber;

(o) loading a solution containing a second fluorescent antibody into the mixing chamber and operating the mixer to mix the solution with the fluid in the mixing chamber, wherein the second fluorescent antibody is labeled with a fluorescent molecule and can bind to the second target;

(p) operating the first bidirectional fluidic channel control unit so that the fluid mixed in step (o) flows from the mixing chamber into the purification chamber;

(q) switching on the magnetic field generating unit so that the magnetic beads contained in the fluid in the purification chamber of step (p) are attracted onto the inner wall of the purification chamber;

(r) operating the waste fluidic channel control unit so that the fluid in the purification chamber flows off via the waste fluidic channel;

(s) loading a resuspension solution into the purification chamber and switching off the magnetic field generating unit so that the magnetic beads are resupeneded in the resuspension solution;

(t) operating the unidirectional fluidic channel control unit of another one of the at least two fluorescence detection units so that the resuspension solution flows from the purification chamber into the fluorescence detection area via the fluorescence detection fluidic channel of the respective fluorescence detection unit; and (u) conducting fluorescence detections of the two fluorescence detection units to determine whether the sample contains the first and/or the second targets.

15. The method of claim 14, wherein the first target and the second target are different bound forms of antigen-antibody complex.

* * * * *